(12) United States Patent
Zatvan et al.

(10) Patent No.: US 10,108,784 B2
(45) Date of Patent: Oct. 23, 2018

(54) SYSTEM AND METHOD OF OBJECTIVELY DETERMINING A USER'S PERSONAL FOOD PREFERENCES FOR AN INDIVIDUALIZED DIET PLAN

(71) Applicants: Oksana Zatvan, Bal Harbour, FL (US); Alexander Zatvan, Moscow (RU); Konstantin Pronko, Moscow (RU); Nikita Pronko, Moscow (RU); Alexey Diashev, Moscow (RU)

(72) Inventors: Oksana Zatvan, Bal Harbour, FL (US); Alexander Zatvan, Moscow (RU); Konstantin Pronko, Moscow (RU); Nikita Pronko, Moscow (RU); Alexey Diashev, Moscow (RU)

(73) Assignee: FACECONTROL, INC., Miami, FL (US)

( * ) Notice: Subject to any disclaimer, the term of this patent is extended or adjusted under 35 U.S.C. 154(b) by 0 days.

(21) Appl. No.: 15/225,167

(22) Filed: Aug. 1, 2016

(65) Prior Publication Data
US 2018/0032701 A1  Feb. 1, 2018

(51) Int. Cl.
*G06F 19/00* (2018.01)
*G06K 9/00* (2006.01)
*G16H 40/63* (2018.01)

(52) U.S. Cl.
CPC .......... *G06F 19/3475* (2013.01); *G06F 19/00* (2013.01); *G06K 9/00302* (2013.01); *G16H 40/63* (2018.01)

(58) Field of Classification Search
CPC ..... G06Q 50/22–50/24; G06F 19/3475; G06F 19/00; G16H 20/70; G16H 20/90; G16H 40/63; G06K 9/00302
See application file for complete search history.

(56) References Cited

U.S. PATENT DOCUMENTS 8,327,395 B2 * 12/2012 Lee .................. G06Q 30/02
                                                     725/10
8,462,996 B2 *  6/2013 Moon ............... G06K 9/00315
                                                     351/203

(Continued)

OTHER PUBLICATIONS

Freeman, Kate. "App Turns Your iPhone's Camera Into a Heartrate Monitor [Video]", Aug. 10, 2012, Mashable, http://mashable.com/2012/08/10/iphone-heartrate-cardiio/#EJfHmM77H8qJ, 2 pgs.*

(Continued)

*Primary Examiner* — Robert A Sorey
(74) *Attorney, Agent, or Firm* — Mark C. Johnson; Johnson |Dalal

(57) ABSTRACT

A computer-implemented method and system is disclosed including automatically displaying each of a plurality of predetermined audio and visual food representations during a predetermined objective food preference determination period at equal time intervals, on a computer display of a computing device. A camera of the computing device automatically captures at least one user-response for each of the equal time intervals corresponding to each of the plurality of predetermined audio and visual food representations. A processing device of the computing device interprets each of the user-responses to determine a user-food preference for each of the plurality of predetermined audio and visual food representations. A personalized diet plan is generated for the user based on the user-food preferences.

20 Claims, 12 Drawing Sheets

(56) References Cited

U.S. PATENT DOCUMENTS

| | | | | |
|---|---|---|---|---|
| 8,473,345 B2* | 6/2013 | Pradeep | | G06Q 30/02 705/14.42 |
| 8,939,903 B2* | 1/2015 | Roberts | | A61B 5/165 600/300 |
| 8,988,350 B2* | 3/2015 | Karmarkar | | G06F 3/013 345/158 |
| 2007/0021168 A1* | 1/2007 | Chamizer | | G06Q 30/08 463/7 |
| 2007/0121066 A1* | 5/2007 | Nashner | | A61B 3/0091 351/210 |
| 2008/0065468 A1* | 3/2008 | Berg | | G06Q 30/02 705/7.32 |
| 2011/0318717 A1* | 12/2011 | Adamowicz | | G09B 19/0092 434/127 |
| 2014/0219526 A1* | 8/2014 | Linguraru | | G06K 9/00281 382/128 |
| 2014/0366049 A1* | 12/2014 | Lehtiniemi | | H04N 21/44218 725/12 |
| 2015/0135309 A1* | 5/2015 | Karmarkar | | G06F 21/36 726/19 |
| 2015/0363860 A1* | 12/2015 | Lantrip | | G06Q 30/0631 705/5 |
| 2015/0374304 A1* | 12/2015 | Gelbman | | G06T 7/0012 600/476 |
| 2016/0012475 A1* | 1/2016 | Liu | | G06F 3/013 705/14.49 |
| 2016/0086500 A1* | 3/2016 | Kaleal, III | | G06T 19/00 434/257 |
| 2016/0103967 A1* | 4/2016 | Bulut | | G16H 40/63 705/2 |

OTHER PUBLICATIONS

Wieringa, F.P., et al., "Contactless Multiple Wavelength Photoplethysmographic Imaging: A First Step Toward "SpO2 Camera" Technology", Annals of Biomedical Engineering, vol. 33, No. 8, Aug. 2005, pp. 1034-1041. (Year: 2005).*

* cited by examiner

500

400

SYSTEM AND METHOD OF OBJECTIVELY DETERMINING A USER'S PERSONAL FOOD PREFERENCES FOR AN INDIVIDUALIZED DIET PLAN

FIELD OF THE INVENTION

The present invention relates generally to dietary plans, and, more particularly, relates to a system and method for objectively determining a user's personal food preferences for an individualized diet plan.

BACKGROUND OF THE INVENTION

Weight loss systems commonly advance the notion that simply limiting a person's food consumption in relation to their energy expenditure and selecting healthy food options will result in weight loss. Typically, a person's diet is recognized as vital to a person's healthy wellbeing. Yet, despite the importance of weight-loss and overall healthy well-being to most people's lives, current weight loss programs are sorely lacking.

Many recommended diet plans are directed towards the physiological requirements of the average person, or people in general, and do not take into consideration an individual's personal food preferences. Some diet plans that address this need to personalize diet plans to an individual provide a wide array of foods from which the individual may choose. Other diet plans may include a user-conducted survey or questionnaire that prompts the user to answer questions about their food preferences in order to individualize the diet plan.

Unfortunately, these types of diet plans are missing a key component, the subconscious. Aside from physiological needs to consume certain types of nutrients found in foods, there are also psychological factors associated with food selection choices, cravings, feelings of satisfaction/satiation, or alternatively, dissatisfaction or avoidance of certain foods. These psychological factors are fairly complex and, frankly, are not entirely understood by scientists and other professionals. A preference for certain foods and, alternatively, distaste or disgust toward other foods are often determined by an individual's unique personal life experience, such as, the individual's upbringing, personal memories, cultural traditions, etc. Addressing such underlying subconscious factors associated with an individual's food consumption choices can be fairly difficult.

One well-known diet is based on points, wherein point values are assigned to each particular food item. The diet requires that the dieter, when the points are added together, not exceed a certain point value. The points relate to a formula which considers the calories, fat and fiber, and other nutritional elements of the food. The diet allows the dieter to select from a wide-range of pre-packaged foods and also provides point values for known food items available at popular restaurants. However, dieters may be overwhelmed by the wide array of choices and the complexity of counting points for every food item consumed. Additionally, dieters may not be aware of the subconscious factors affecting their food choices and may, therefore, become frustrated and baffled by their conscious decisions to consume foods beyond their allotted point value, or otherwise not meeting the requirements of the diet plan. Addressing only the dieter's conscious decision-making factors, as with conventional dietary plans, leaves out an important component of the dieter's underlying biological and subconscious decision-making processes, setting dieters up for eventual failure.

In order to adhere to a dietary plan on a consistent basis, it is known to provide the dieter with healthy foods that the dieter also enjoys. Unfortunately, like many people, dieters are often unaware of or naive to their personal food preferences. Dieters may make food selection choices based on what is socially or culturally acceptable. For example, the dieter may choose a salad for lunch as a socially acceptable "healthy" food choice. However, such dieter may actually objectively dislike salads; yet, be unaware of or naive to such fact. Accordingly, the dieter may not understand why she is unable to adhere to her dietary plan. A need exists in the weight-loss and dietary plan arts to objectively identify dieters' personal food preferences in order to generate a personalized diet plan that objectively determines dieters' true food preferences based on objective criteria.

Therefore, in spite of the myriad of existing dietary plans, a need exists to overcome the problems with the prior art as discussed above. Namely, a need exists for a system and method for objectively determining a user's personal food preferences for an individualized diet plan.

SUMMARY OF THE INVENTION

The invention provides a system and method for objectively determining a user's personal food preference for an individualized diet plan that overcomes the hereinafore-mentioned disadvantages of the heretofore-known devices and methods of this general type.

With the foregoing and other objects in view, there is provided, in accordance with the invention, a computer-implemented method of objectively determining a user's personal food preferences for an individualized diet plan. The method includes providing at least one database storing a plurality of predetermined digital food images, the at least one database communicatively coupled to a processing device of a personal computing device, the personal computing device further including a digital camera, a memory, a computer display, and a user-input interface communicatively coupled to one another. After the step of providing the at least one database having stored thereon the plurality of predetermined digital food images, a user-input interface on the personal computing device receives an indication from a user to begin a predetermined objective food preference determination period. During the predetermined objective food preference determination period, each of the plurality of predetermined digital food images is automatically displayed on the computer display of the personal computing device at equal time intervals. During each of the equal time intervals, the digital camera disposed at the personal computing device automatically captures at least one visual user-response of the user for each of the plurality of predetermined digital food images displayed on the computer display during the predetermined objective food preference determination period. Each of the at least one visual user-responses captured during each of the equal time intervals within the predetermined objective food preference determination period is stored in the memory. The processing device of the personal computing device may interpret each of the at least one stored visual user-responses captured during the predetermined objective food preference determination period to determine a user-food preference for each of the plurality of predetermined digital food images displayed on the computer display. After the step of interpreting each of the at least one stored visual user-responses, the processing device of the personal computing device generates an individualized diet plan for the user based on the user-food preference for each of the plurality of predetermined digital food images.

In accordance with another feature of the present invention, each of the equal time intervals is between 0.233 and 0.385 seconds.

In accordance with yet another feature of the present invention, each of the plurality of predetermined digital food images is formed as a computer displayable image in which a single food item occupies a substantial portion of the entire computer displayable image.

In accordance with yet another feature of the present invention, the digital camera is operable to capture at least one image of the at least one visual user-response with a pixel resolution of at least 640×480 pixels.

In accordance with another feature, an embodiment of the present invention includes prompting, by the personal computing device, the user to be physically disposed in front of a camera lens of the digital camera within a single separation distance from the camera lens and simultaneously within a viewing distance of the computer display during the entire predetermined objective food preference determination period.

In accordance with another feature of the present invention, the step of automatically displaying each of the plurality of predetermined digital food images, further includes automatically displaying each of the plurality of predetermined digital food images in a continuous sequence during the predetermined objective food preference determination period.

In accordance with an additional feature of the present invention, generating the individualized diet plan further includes a step of generating a list of food items to exclude from the user's individualized diet plan, the list of food items including at least one food item depicted in the plurality of predetermined digital food images displayed on the computer display during the predetermined objective food preference determination period that were determined, during the interpreting step, to have a user-food preference associated with a negative emotional user-response.

In accordance with yet another feature, an embodiment of the present invention includes providing the database with a plurality of predetermined food items stored thereon from which the individualized diet plan is generated in the generating step. The step of generating the individualized diet plan may further includes a step of hierarchically ranking, by the processing device, each food item depicted in the plurality of digital food images displayed on the computer display during the automatically displaying step, the hierarchical ranking based on a hierarchal level of the user-food preferences determined in the interpreting step.

In accordance with yet another feature, an embodiment of the present invention includes determining a pulse of the user during each of the equal time intervals by interpreting the visual user-response captured during the respective equal time interval, the pulse of the user represented in the captured visual user-response; and determining a facial expression of the user during each of the equal time intervals by interpreting the visual user-response captured during the respective equal time interval, the facial expression of the user depicted in the captured visual user-response.

In accordance with another feature of the present invention, each of the equal time intervals are equally-spaced apart from one another.

In accordance with yet another feature of the present invention, before the predetermined objective food preference determination period, during a predetermined user calibration period, the digital camera disposed at the personal computing device automatically captures at least one visual user-response of the user. Further, the processing device of the personal computing device may interpret the visual user-responses captured during the predetermined user calibration period to determine a baseline user response, wherein each of the user-food preferences determined during the interpreting step of the predetermined objective food preference determination period is determined based on the baseline user response.

In accordance with another feature, an embodiment of the present invention includes a method of objectively determining a user's personal food preferences for an individualized diet plan, the method includes providing at least one database storing at least one of a plurality of predetermined audio and visual food representations, the at least one database communicatively coupled to a processing device of a personal computing device, the personal computing device further including a digital camera, a computer display, a user-input interface, and a speaker communicatively coupled to one another. After the step of providing the at least one database having stored thereon at least one of the plurality of audio and visual food representations, a user-input interface on the personal computing device receives an indication from a user to begin a predetermined objective food preference determination period. During the predetermined objective food preference determination period, the method also includes at least one of 1) automatically displaying, on the computer display of the personal computing device, each of the plurality of predetermined visual food representations and 2) automatically emitting, via the speaker, the plurality of predetermined audio food representations, at equal time intervals. During each of the equal time intervals, the digital camera disposed at the personal computing device automatically captures at least one user-response of the user for each of the at least one of the plurality of predetermined audio and visual food representations. The processing device of the personal computing device interprets each of the user-responses captured during the predetermined objective food preference determination period to objectively determine a user-food preference for each of the at least one of the plurality of predetermined audio and visual food representations. After the step of interpreting each of the at least one user-responses, the processing device of the personal computing device generates an individualized diet plan for the user based on the user-food preferences for each of the plurality of audio and/or visual food representations.

In accordance with a further feature of the present invention, the method includes, after the step of providing the database having stored thereon at least one of the plurality of audio and visual food representations, prompting the user to be physically disposed in front of a camera lens of the digital camera within a single separation distance from the camera lens and simultaneously within at least one of a viewing distance of the computer display and a listening distance from the speaker during the entire predetermined objective food preference determination period.

In accordance with another feature of the present invention, each of the plurality of audio and visual food representations includes a plurality of predetermined digital food images formed as a computer displayable image in which a single food item occupies a substantial portion of the entire computer displayable image.

In accordance with another feature, an embodiment of the present invention includes a system for objectively determining a user's personal food preferences for an individualized diet plan, the system having at least one database storing at least one of a plurality of predetermined audio and visual food representations; and a personal computing device communicatively coupled to the at least one database and including a processing device, a computer display, a speaker, a non-transitory memory, a user-input interface, and a digital camera communicatively coupled to one another and having a set of computer instructions stored in the non-transitory memory and executable by the processing device. The set of computer instructions may, in accordance with another feature of the present invention, include instructions for receiving, by the user-input interface on the personal computing device, an indication from a user to begin a predetermined objective food preference determination period; during the predetermined objective food preference determination period, at least one of automatically displaying, on the computer display of the personal computing device, each of the plurality of predetermined visual food representations and automatically emitting, via the speaker, the plurality of predetermined audio food representations, at equal time intervals; and during each of the equal time intervals, automatically capturing, by the digital camera, at least one user-response of the user for each of the at least one of the plurality of predetermined audio and visual food representations output during the predetermined objective food preference determination period. The set of computer instructions may, in accordance with a further embodiment, include instructions for storing, in the non-transitory memory, each of the at least one user-responses captured during each of the equal time intervals within the predetermined objective food preference determination period; interpreting, by the processing device, each of the at least one stored user-responses captured during the predetermined objective food preference determination period to determine a user-food preference for each the at least one of the plurality of predetermined audio and visual food representations; after the step of interpreting each of the at least one stored user-responses, generating, by the processing device, an individualized diet plan for the user based on the user-food preferences for each of the at least one of the plurality of predetermined audio and visual food representations; and displaying, on the computer display, the diet plan.

Although the invention is illustrated and described herein as embodied in a system and method for objectively determining a user's personal food preference for an individualized diet plan, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of a personal computing device from one terminating end to an opposing terminating end. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
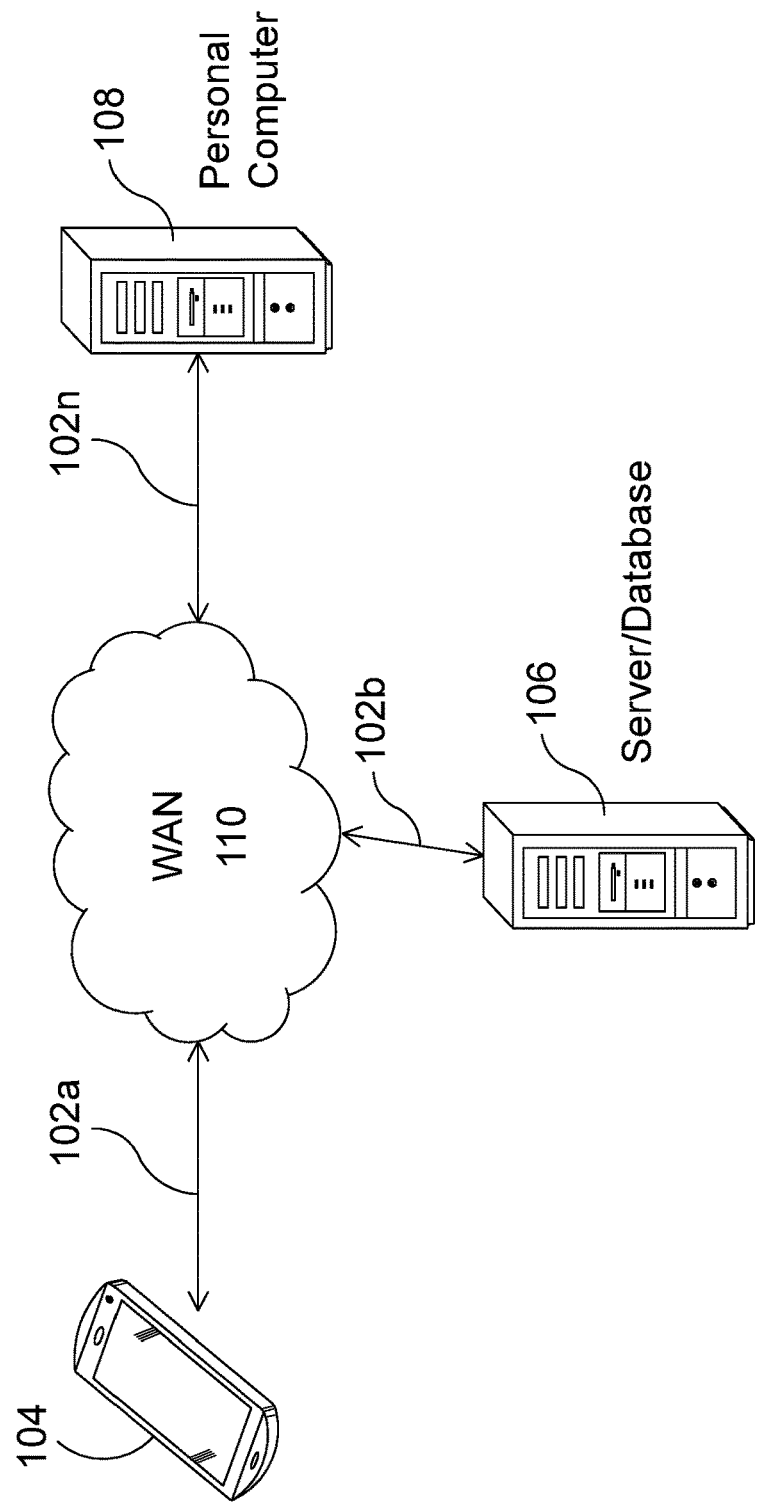
FIG. 1 is a block diagram of an exemplary distributed data processing network with a personal mobile computing device, a personal computer (PC), and a server/database in accordance with an embodiment of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient computer-implemented method and system that objectively determines a user's personal food preferences based on exposing the user to audio and/or visual food stimulus and detecting the user's biological responses via biological sensors. Embodiments of the invention provide for generating a personalized diet plan for the user that eliminates food items that are objectively determined to be distasteful to the user, or that the user otherwise has a negative association with. In addition, embodiments of the invention provide for exposing the user to a plurality of audio and/or visual food stimuli within a predetermined food display period, via the user's personal computing device, in very short time intervals in order to obtain the user's most instinctive biological response to the stimuli.

Referring now to FIG. 1, one embodiment of the present invention is shown as a block diagram, illustrating an exemplary network of data processing system in which the present invention may be implemented. FIG. 1 shows several advantageous features of the present invention, but, as will be described below, the invention can be provided in several shapes, sizes, combinations of features and components, and varying numbers and functions of the components. The first example of a network 100, as shown in FIG. 1, includes connections 102a-n, which are the medium used to provide communication links between various devices and computers connected together within the network 100. The connections 102a-n may be wired or wireless connections. A few exemplary wired connections are cable, phone line, and fiber optic. Exemplary wireless connections include radio frequency (RF) and infrared radiation (IR) transmission. Many other wired and wireless connections are known in the art and can be used with the present invention.

In the depicted example, the network 100 includes a personal mobile computing device 104, a server 106, and a personal computer 108. The personal mobile computing device 104 can be operable to execute programming instructions embodied in a software application that can be received from the server 106 via a wide area network (WAN) 110. In other embodiments, the personal computer 108 is operable to execute the programming instructions received from the server 106 over the WAN 110. In yet other embodiments, the software application is a web-based software application, a desktop software application, or a mobile device software app. In one embodiment, the WAN is the Internet. The Internet represents a worldwide collection of networks and gateways that use the TCP/IP suite of protocols to communicate with one another. At the heart of the Internet is a backbone of high-speed data communication lines between major nodes or host computers, consisting of thousands of commercial, government, educational and other computer systems that route data and messages. Of course, the network 100 also may be implemented as a number of different types of networks, such as for example, an Intranet, a local area network (LAN), or a cellular network. FIG. 1 is intended as an example, and not as an architectural limitation for the present invention.

The server 106 can be seen as a computer that manages access to a centralized resource or database. In some embodiments, users of personal mobile computing device 104 can request the software application embodying an exemplary method of the present invention. The server 106 can receive, process, and satisfy the request by sending the software application to the personal mobile computing device 104 via the WAN 110. In yet other embodiments, the personal computer 108 can request the software application and the server 106 can receive, process, and satisfy the request by sending the software application to the personal computer 108 via the WAN 110.

Figure 2:
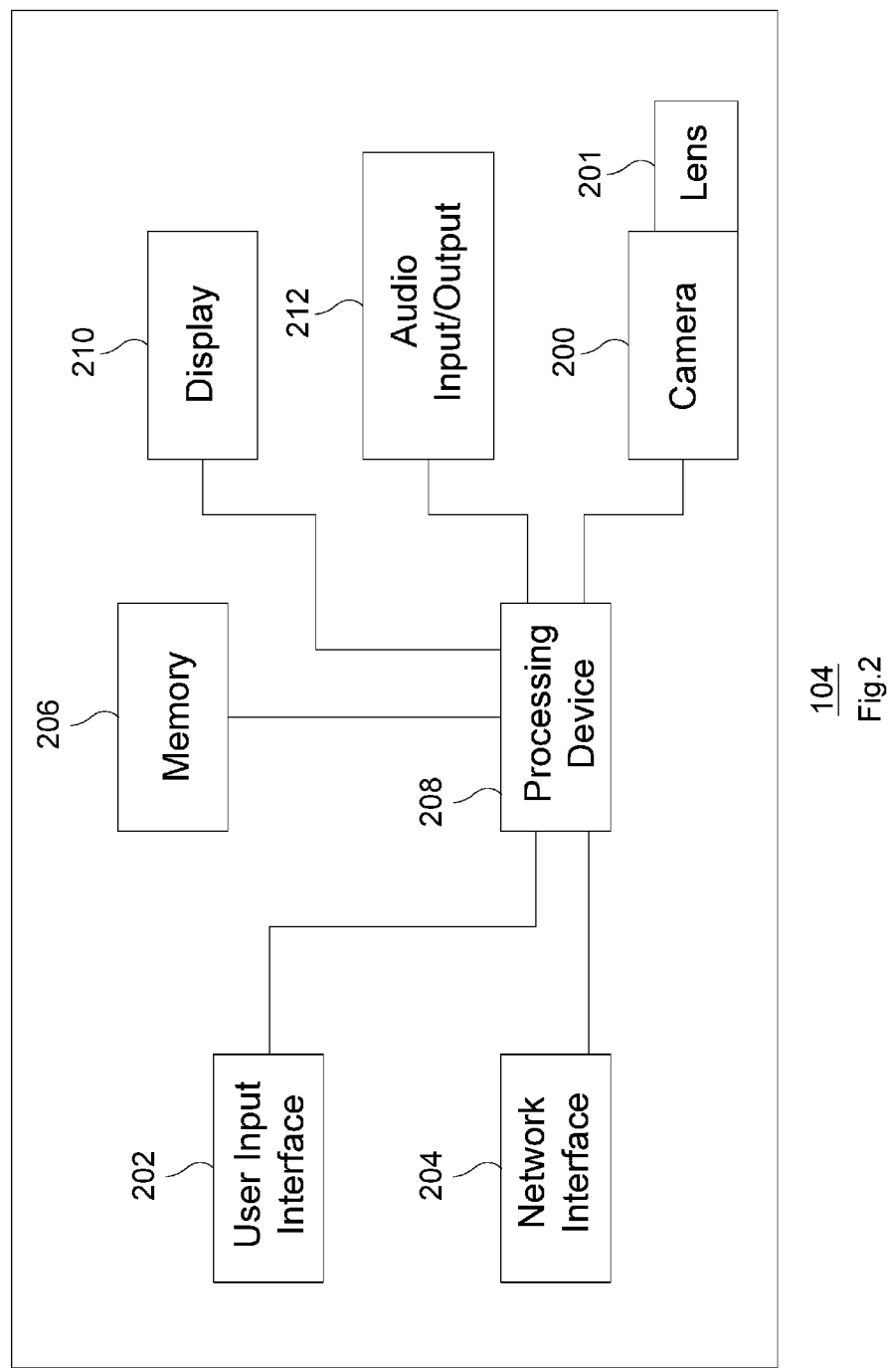
FIG. 2 is a block diagram of an exemplary personal mobile computing device in accordance with the present invention.

With reference now to FIG. 2, the personal computing device 104 is illustrated in a block diagram. The personal computing device 104 includes a camera 200, a user input interface 202, a network interface 204, a memory 206, a processing device 208, a computer display 210, and an audio input/output 212.

The camera 200 may include a camera lens 201 and may be operable to capture still images, as well as, video. The camera 200 is preferably a digital camera so that the images may be stored in the memory 206 and processed by the processing device 208. The camera 200 may be communicatively coupled to a microphone for capturing audio, as well as, simultaneous visual video images. The camera 200 is preferably operable to capture images having a pixel resolution of at least 640×480 pixels in order to provide a high resolution image for interpretating and analyzing the images in accordance with techniques described herein, and generally known in the art. Cameras having a lesser quality may not be operable to provide high resolution images that may be required to accurately determine a user-food preference from captured images within a reasonable degree of error.

The user input interface 202 functions to provide the user a method of providing input to the personal computing device 104. The user input interface 202 may also facilitate interaction between the user and the device 104. The user input interface 202 may be a keypad providing a variety of user input operations. For example, the keypad may include alphanumeric keys for allowing entry of alphanumeric information (e.g. telephone numbers, contact information, text, etc.). The user input interface 202 may include special function keys (e.g. a camera shutter button, volume control buttons, back buttons, home button, etc.), navigation and select keys, a pointing device, and the like. Keys, buttons, and/or keypads may be implemented as a touchscreen associated with the computer display 210. The touchscreen may also provide output or feedback to the user, such as haptic feedback or orientation adjustments of the keypad according to sensor signals received by motion detectors, such as an accelerometer, located within the device 104.

The network interfaces 204 may include one or more network interface cards (NIC) or a network controller. In some embodiments, the network interface 204 may include a personal area network (PAN) interface. The PAN interface may provide the capability for the personal computing device 104 to network using a short-range communication protocol, for example, a Bluetooth communication protocol. The PAN interface may permit one personal computing device 104 to connect wirelessly to another personal computing device 104 via a peer-to-peer connection.

The network interfaces 204 may also include a local area network (LAN) interface. The LAN interface may be, for example, an interface to a wireless LAN, such as a Wi-Fi network. The range of the LAN interface may generally exceed the range available via the PAN interface. Typically, a connection between two electronic devices via the LAN interface may involve communication through a network router or other intermediary device.

Additionally, the network interfaces 204 may include the capability to connect to a wide area network (WAN) via a WAN interface. The WAN interface may permit a connection to, for example, a cellular mobile communications network. The WAN interface may include communications circuitry, such as an antenna coupled to a radio circuit having a transceiver for transmitting and receiving radio signals via the antenna. The radio circuit may be configured to operate in a mobile communications network, including but not limited to global systems for mobile communications (GSM), code division multiple access (CDMA), wideband CDMA (WCDMA), and the like.

The personal computing device 104 may also include a near field communication (NFC) interface. The NFC interface may allow for extremely close range communication at relatively low data rates (e.g., 424 kb/s). The NFC interface may take place via magnetic field induction, allowing the NFC interface to communicate with other NFC interfaces located on other mobile computing devices 104 or to retrieve information from tags having radio frequency identification (RFID) circuitry. The NFC interface may enable initiation and/or facilitation of data transfer from one personal computing device 104 to another computing device 104 with an extremely close range (e.g. 4 centimeters).

Memory 206 associated with the device 104 may be, for example, one or more buffer, a flash memory, or non-volatile memory, such as random access memory (RAM). The personal computing device 104 may also include non-volatile storage. The non-volatile storage may represent any suitable storage medium, such as a hard disk drive or non-volatile memory, such as flash memory.

The processing device 208 can be, for example, a central processing unit (CPU), a microcontroller, or a microprocessing device, including a "general purpose" microprocessing device or a special purpose microprocessing device. The processing device 208 executes code stored in memory 206 in order to carry out operation/instructions of the personal mobile computing device 104. The processing device 208 may provide the processing capability to execute an operating system, run various applications, and provide processing for one or more of the techniques described herein.

The computer display 210 displays information to the user such as an operating state, time, telephone numbers, various menus, application icons, pull-down menus, and the like. The computer display 210 may be used to present various images, text, graphics, or videos to the user, such as photographs, mobile television content, Internet webpages, and mobile application interfaces. More specifically, the display 210 may display food images/video and individualized dietary plans. The computer display 210 may be any type of suitable display, such as a liquid-crystal display (LCD), a plasma display, a light-emitting diode (LED) display, or the like.

The personal computing device 104 may include audio input and output structures 212, such as a microphone for receiving audio signals from a user and/or a speaker for outputting audio signals, such as audio recordings associated with food (e.g., a person chewing the food), and the like. The personal computing device 104 may also include an audio port for connection to peripheral audio input and output structures, such as a headset, or peripheral speakers or microphones.

Figure 3:
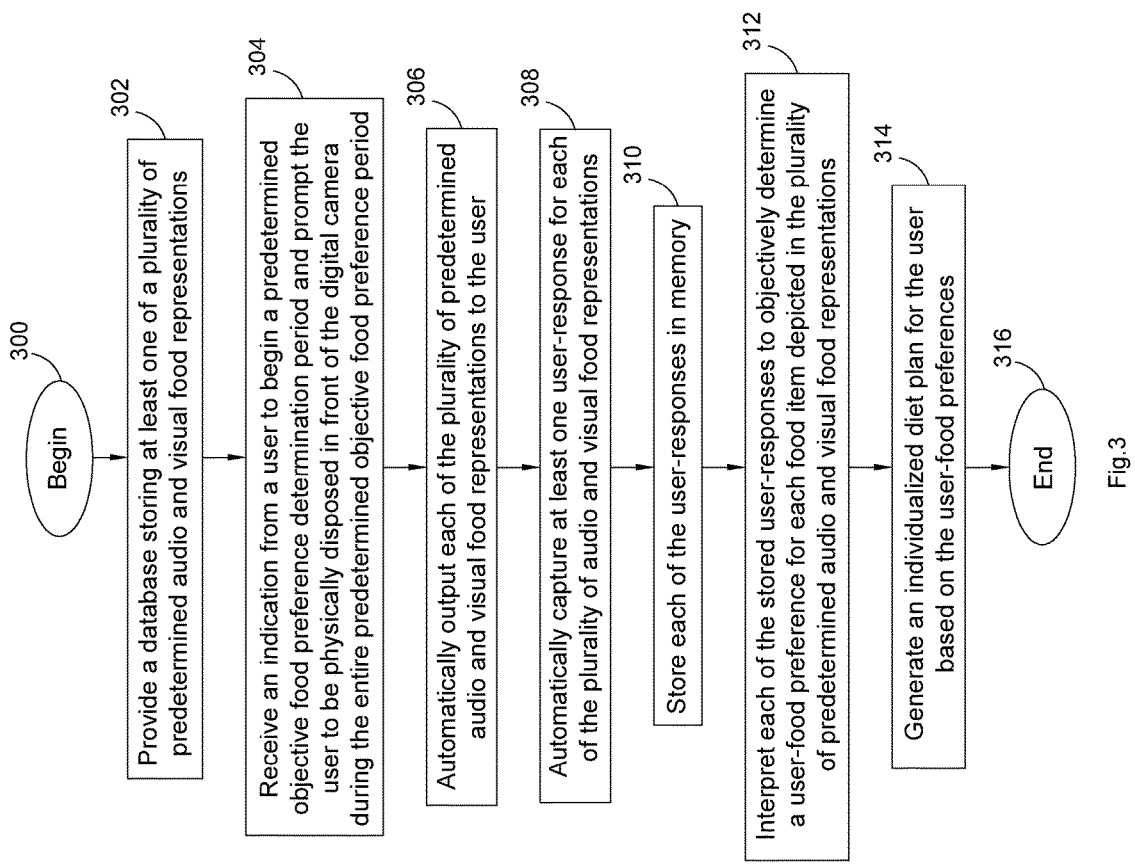
FIG. 3 is a process flow chart representing an exemplary method of objectively determining a user's personal food preference to generate an individualized diet plan for the user in accordance with an embodiment of the present invention.
Figure 5:
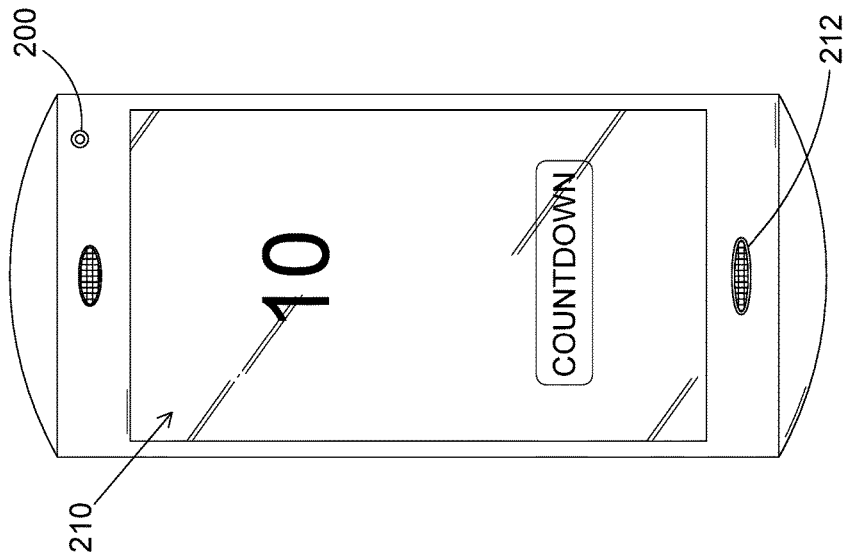
FIG. 5 is a screenshot from the exemplary software application of FIG. 4 depicting a user interface displaying a countdown message to begin the food display period in accordance with an embodiment of the present invention.

FIGS. 1-2 and 4-15 will be described in conjunction with the process flow chart of FIG. 3. Although FIG. 3 shows a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIG. 3 for the sake of brevity. In some embodiments, some or all of the process steps included in FIG. 3 can be combined into a single process.

The exemplary process, depicted in FIG. 3, begins at step 300 and immediately proceeds to step 302, where a database is provided storing at least one of a plurality of predetermined audio and visual food representations 600, separately, concurrently, and/or sequentially. In one embodiment, the database is the server 106, or otherwise communicatively coupled to the server 106. In a preferred embodiment, the database is at least a portion of the memory 206 (preferably non-transitory memory) on the personal mobile computing device 104. This embodiment allows the plurality of predetermined audio and/or visual food representations 600 to be very quickly exposed to the user in short intervals so as to obtain the most instinctive, subconscious biological user response to the food representation stimuli. As is known in the art, displaying images or playing/outputting/emitting audio can more quickly be performed by accessing a computing device's local memory, rather than attempting to access the files from a remote database or server, across a network.

The database is communicatively coupled to the processing device 208 of the personal mobile computing device 104. In an embodiment in which the database is considered at least a portion of the memory 206 on the personal computing device 104, such communicative coupling may be a hard-wired conductive connection. In an embodiment in which the database is considered a remote database 106 accessible over, for example, a long-distance network, such as the WAN 110, such communicative coupling may be via the network interface 204 on the personal mobile computing device 104. The term "database" is intended in a broad sense to mean an organized collection of data that is stored in a non-transitory-type memory and is accessible by a processing device for utilizing the collection of data to perform computer processing tasks.

The plurality of predetermined audio and/or visual food representations 600 may be formed as, for example, a still digital image of a food item, a video of a food item with audio and visual, and an audio only representation of a food item (e.g., an audio file of the food item being consumed). As used herein, the phrase "predetermined food representation" is intended to indicate that the food representation is determined before providing said representation to the user (and is often times not selected or chosen by the user) and is stored in a non-transitory memory so that a processor can access the computer-stored food representation from the non-transitory memory for output on a computer or computer component in a manner that is understandable to a human being, i.e., displayed on a computer display, in the case of a visual representation, and emitted via a speaker, in the case of an audio representation. This should be apparent to a person of ordinary skill in the art.

As used herein, the term "visual food representation" is intended to indicate a computer-displayable depiction of a food item. In preferred embodiments, the predetermined visual food representation 600 is formed as a digital still image (e.g., photograph), or a moving image (e.g., digital video) primarily depicting the food item so that the user-response can be clearly linked to the food item. In other words, the predetermined visual food representations 600 should not include other depictions, or may only include nominal non-food depictions (e.g., a plate or bowl on which the food items rests or a simple background color). In a more preferred embodiment, each of the plurality of predetermined visual food representations 600 displayed for the user has a consistent background (e.g., white background) across each food representation so that user-response can be clearly linked to the food item depicted. In other words, depicting other non-food items may result in an erroneous user-response determination in which the user's response is actually a result of the non-food item.

In one embodiment, each of the plurality of predetermined visual food representations 600 includes a plurality of predetermined digital food images formed as a computer-displayable image in which a single food item occupies a substantial portion of the entire computer displayable image. As used herein, the term "food item" is intended broadly to be inclusive of foods, as well as, consumable fluids, and that include foods of only a single ingredient (e.g., broccoli, or milk) and meals that include multiple ingredients (e.g., a summer salad). As used herein, the phrase "substantial portion of the entire computer-displayable image" is intended to indicate that at least 75% of the entire computer-displayable image depicts the food item. It should be understood that in preferred embodiments the food representations are primarily depictions of food so that the user-response can be attributed to the food being depicted and not other non-food items (e.g., people, nature, etc.). In other embodiments, the food item may occupy less than, or more than 75% of the entire computer-displayable image(s).

As used herein, the term "audio food representation" is intended to indicate an audio representation of an audio aspect of a food item that can be output via a speaker. In preferred embodiments, the predetermined audio food representation 600 is formed as a digital audio file that primarily audibly represents the food item so that the user-response can be clearly linked to the food item. In other words, the predetermined audio food representations 600 should not include other sounds, or may only include nominal non-food related sounds.

Figure 4:
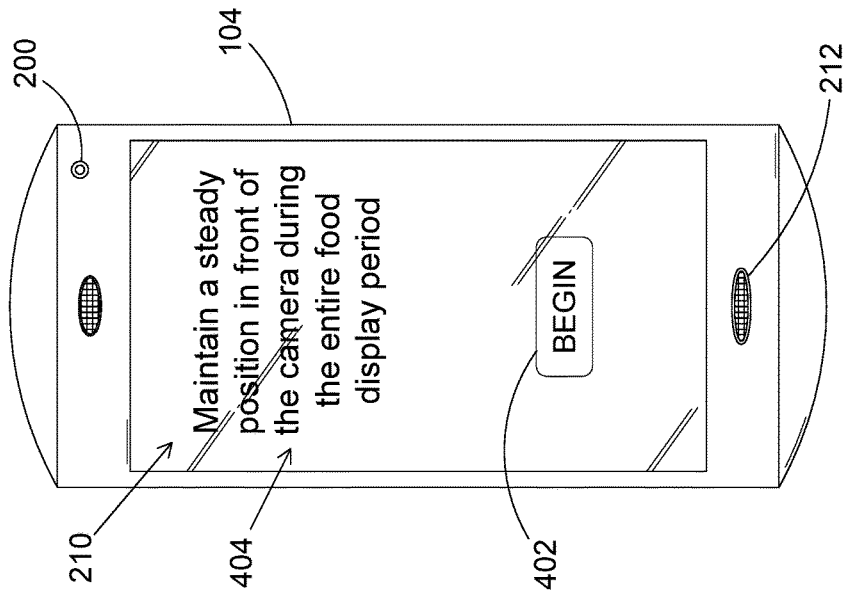
FIG. 4 is a screenshot of an exemplary software application at least partially implementing the inventive process, the screenshot depicting a user initiation screen to begin a food display period on the personal mobile computing device in accordance with an embodiment of the present invention.
Figure 6:
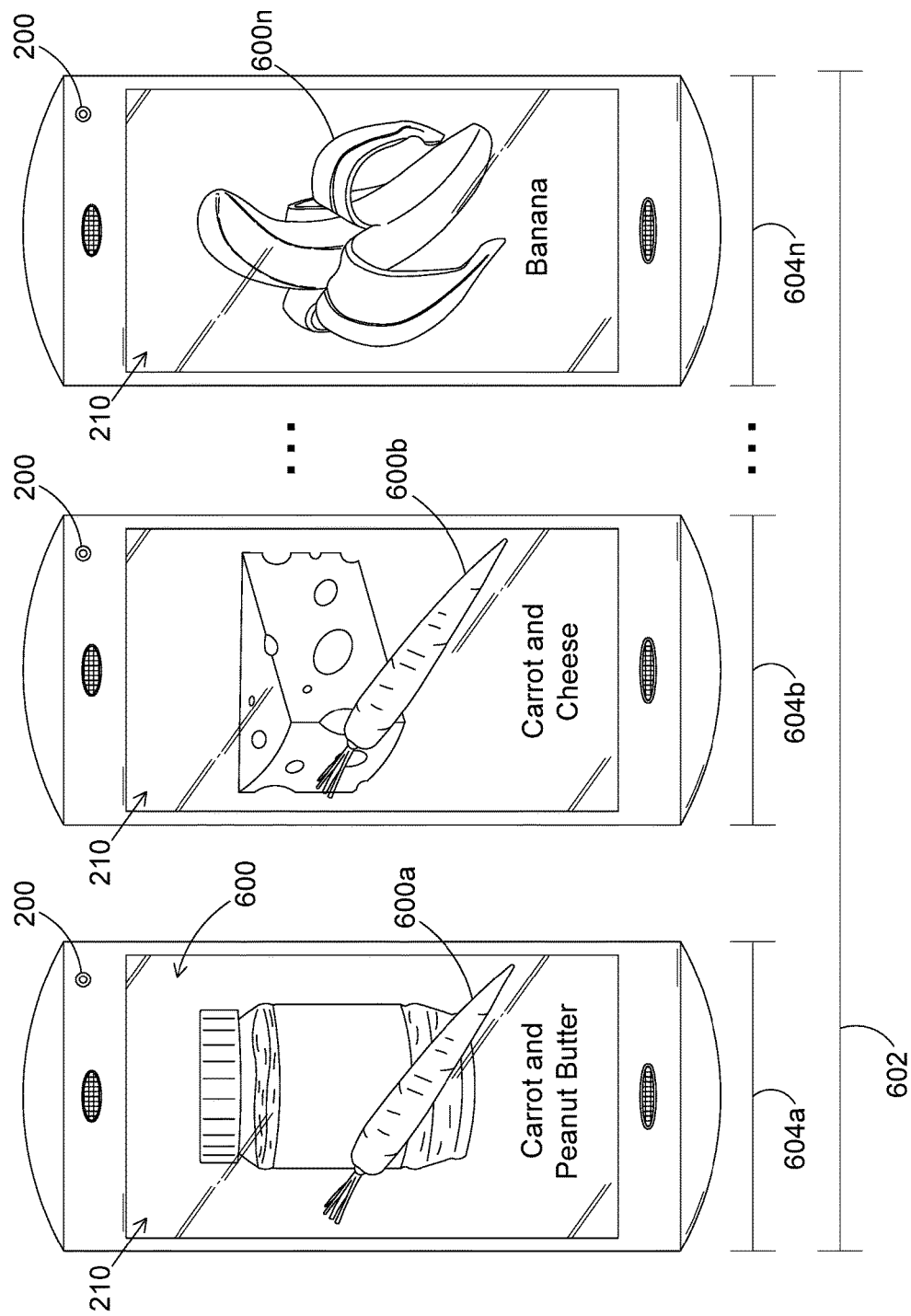
FIG. 6 is a sequence of screenshots from the exemplary software application of FIG. 4 depicting various food images displayed on the personal mobile computing device in accordance with an exemplary embodiment of the present invention.

In step 304, an indication is received from a user to begin a predetermined objective food preference determination period 602. The indication from the user to begin the predetermined objective food preference determination period 602 is received via the user-input interface 202 on the personal computing device 104. FIG. 4 depicts an exemplary screenshot 400 of a user-interface in which the user is provided with a "begin" button 402 that the user may select to indicate that the user is ready to begin receiving audio and/or visual food representations 600. It should be understood by persons of ordinary skill in the art that there are a number of other ways in which the user may input a "begin" or other initiation-type command, such as, an audio voice recognition command, or other methods and structures for inputting a user command into the personal computing device 104. In a further embodiment, as illustrated in the screenshot 500 depicted in FIG. 5, after the user inputs a command to begin the predetermined objective food preference determination period 602, the display 210 and/or audio output 212 may countdown or otherwise prepare the user to position himself/herself correctly prior the predetermined objective food preference determination period 602. In the exemplary embodiment, the display 210 counts down from 10 to give the user 10 seconds to position himself/herself correctly. It is important that the user physically position himself/herself correctly so as to be able to receive the audio and/or visual food representations 600 and for the camera 200 to be able to capture the user's responses during the predetermined objective food preference determination period 602.

Figure 7:
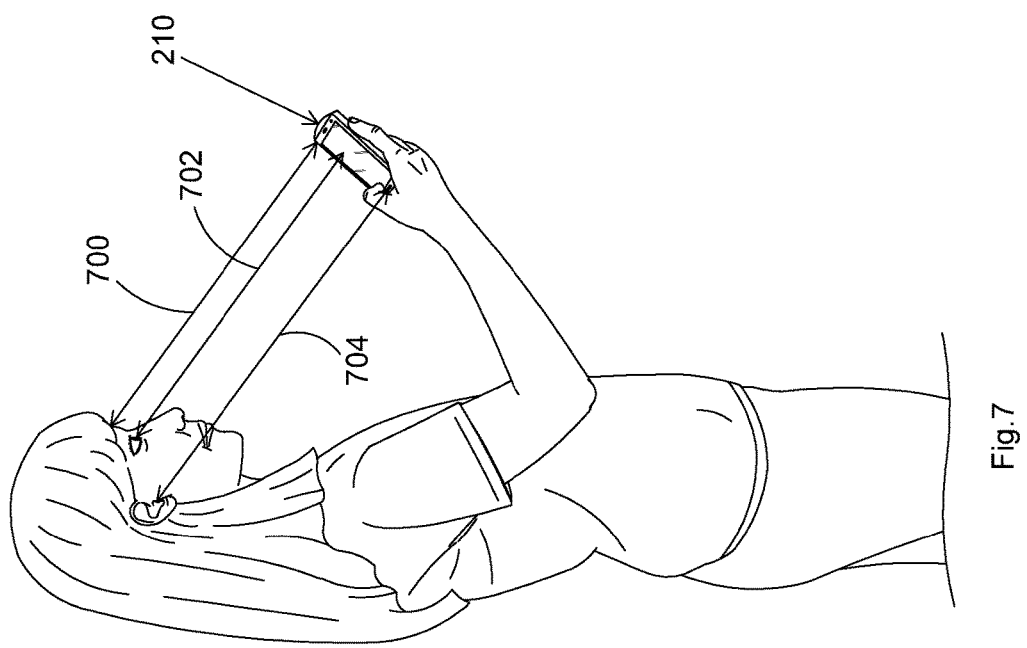
FIG. 7 is a schematic diagram of a user physically disposed in front of a camera lens of a camera disposed on the personal mobile computing device in accordance with an embodiment of the present invention.

During the predetermined objective food preference determination period 602, while audio and/or visual food representations 600 are being output to the user, the user should remain within a consistent distance from the camera lens 201 of the camera 200. In one embodiment, the user may be prompted by the personal computing device 104 to be physically disposed in front of the camera lens 201 of the camera 200 within a single separation distance 700, as illustrated in FIG. 7. The user should also simultaneously be physically disposed within a viewing distance 702 of the display 210 (for visual food representations) and/or within a listening distance 704 from the audio output/speaker 212, during the entire predetermined objective food preference determination period 602. The prompting by the personal computing device 104 may be, for example, a visual message 404 displayed on the display 210 and/or an audio message output via the audio output 212 of the personal computing device 104.

Similar to the phrase, "predetermined food representation," the phase "predetermined objective food preference determination period 602" is intended to indicate that the objective food preference determination period is determined before outputting the audio and/or visual food representations 600 to the user and is stored in a non-transitory memory so that the processing device 208 can be instructed as to when to begin and/or end the period.

In step 306, during the predetermined objective food preference determination period 602, the personal computing device 104 outputs each of the plurality of audio and/or visual food representations 600 to the user. In one embodiment, the personal computing device 104 may automatically display on the display 210 each of the predetermined visual food representations 600. Said another way, personal computing device 104 causes, directly or indirectly, each of the predetermined visual food representations 600 to be depicted on the display 210 without constant user-intervention typically associated with known dieting software applications. In another embodiment, the personal computing device 104 may automatically play, via the speaker 212, each of the predetermined audio food representations 600. In yet another embodiment, during the predetermined objective food preference determination period 602, the personal computing device 104 may automatically play on the display 210 and speaker 212 a video (with simultaneous audio) of the predetermined visual and audio food representations 600.

In a preferred embodiment, the outputting of each of the plurality of audio and/or visual food representations 600 should occur at equal time intervals 604a-n, or a period of time in which each representation 600 is depicted. "Equal" is defined as being substantially equal, or within +/− one-second deviation of one another. In a further embodiment, each of the equal time intervals 604a-n may be equally-spaced apart from one another. In other words, the time-spacing between each of the equal time intervals 604a-n may be equal, as well. Such equal spacing between the equal time intervals 604a-n may be, example, 0 seconds to several seconds (e.g., 1-3 seconds). This provides for a controlled and consistent user-response. In other words, by keeping all variables, except the food items constant, i.e., control variables, the user-response can be more accurately determined as a result of the particular food item. In a further preferred embodiment, the equal time intervals 604 within which the food items are output to the user are kept relatively short, so as to obtain a more instinctive user response to the food items. The number of equal time intervals "a" through "n" can be any number. Specifically, the number of equal time intervals 604 should correspond to the number of predetermined audio and/or visual food representations 600 output to the user during the predetermined objective food preference determination period 602. In yet another preferred embodiment, each of the equal time intervals 604 are between 0.233 and 0.385 seconds. In other embodiments, the equal time intervals 604 may be outside of this range, but should still provide a relatively short duration so as to obtain an instinctive biological user response, preferably without permitting the user's conscious mind to alter his/her user-response to the output.

In one embodiment, each of the plurality of predetermined audio and/or visual food representations 600 is output during the predetermined objective food preference determination period 602 in a continuous, uninterrupted sequence of food representations. In an alternative embodiment, there may be a short time interval between each output of the audio and/or visual food representations 600. In such embodiments, the time interval between outputs of the audio and/or visual food representations 600 should be the same so as to still remain generally uniformly presented to the user. As used herein, the term "continuous" is intended to mean that each of the plurality of predetermined audio and/or visual food representations 600 is output to the user as a continuous sequence of food representations, without any other images or audio interposed therebetween. Some embodiments may include very nominal images or audio interposed therebetween, such as, black or white screen pauses between food representations. In the exemplary embodiment depicted in FIG. 6, the plurality of predetermined audio and/or visual food representations 600a-n are illustrated as depicting different food items within equal time intervals 604a-n. The number of predetermined audio and/or visual food representations "a" through "n" can be any number. Generally, each of the plurality of predetermined audio and/or visual food representations 600a-n should be different from one another, although some of the depicted food items may contain common ingredients.

In step 308, during each of the equal time intervals 604a-n, the camera 200 automatically captures at least one user-response 800 of the user for each of the predetermined audio and/or visual food representations 600a-n. In one embodiment, the user-response is a considered a visual user-response 800 and may be captured as a video, and/or one or more still digital images of the user. In a further embodiment, the visual user-response 800 may be formed as at least two chronological still images captured within the respective equal time interval 604. In one embodiment, the visual user-response 800 captured by the camera 200 includes a video and/or one or more still digital images of the user's face 802. In other embodiments, the visual user-response 800 captured by the camera 200 may also depict other physical body parts of the user from which biological/physiological user responses can be identified and interpreted. The camera 200 may be operable as a sensor to determine a user-response to each of the predetermined audio and/or visual food representations 600a-n output to the user during the predetermined objective food preference determination period 602. In other embodiments, the personal computing device 104 may include other sensors operable to capture the physiological/biological state of the user so as to determine the user's objective food preference.

The physiological state may be associated with a property or function of the user's skin, or any of the circulatory, digestive, lymphatic, respiratory, reproductive, skeletal, muscular, excretory, endocrine, or nervous systems, including brain function, or paralanguage of a mammal, alone or in combination. The physiological state may also be associated with paralanguage which can include body language and voice inflection—which are a response to muscular and micro-muscular movements and conditions. The physiological response may be measured using the methods and equipment for making such measurements as are known in the art. The scaled emotional state may be derived utilizing methods described in U.S. patent application Ser. No. 11/851,638, incorporated herein by reference. Additionally, exemplary methods for deriving a scaled emotional state include skin galvanic response, pulse and blood pressure measurement, respiration rate, facial expression, and layered voice analysis. The methods and equipment for making such measurements can include non-contact sensors, contact sensors, and sampling approaches to obtaining user-response measurements. Non-contact approaches include sensors that do not contact the user's body. Examples of such non-contact sensors includes IR reflectance of pupil size, saccade paths, or eyelid blink behavior; remote microphones for capturing the user's voice; skin temperature or coloration measurements via, for example, thermography; heart rate or respiration determination by radar and/or Doppler-based analysis as provided in and incorporated herein by reference WO/2007/1143535 entitled "Apparatus, System, and Method for Monitoring Physiological Signs," and WO 2007/1148865 entitled "Method for Radio Physiological Signal Biometric and Radio Physiological Signal System and Using the Same."

Contact approaches have at least one sensor or other measurement device that is disposed in physical contact with the user's body. Examples of such contact sensors include ocular measuring glasses measuring pupil size, saccade paths, or eyelid blink behavior; skin temperature sensors; blood pulse sensors; respiratory rate sensors; galvanic skin sensors; EEG (electroencephalograph) equipment, such as, in helmet form for measuring brain activity; EMG (electromyogram) muscle and muscle set sensors used to detect movement or tension of muscles, such as, facial muscles; ECG or EKG (electrocardiogram) to measure cardio electrical signals; sound wave techniques such as echocardiogram to produce images of the heart; etc. Such sensors can be tethered to other equipment or data loggers, or transmit data or information wirelessly. Such sensors can also include data logging or analysis functionality, either as part of the sensor, or connected via wires, or wirelessly, to a separate component or equipment. Examples of neuro-response measurements include EEG, galvanic skin response (GSR), EKGs, electrooculography (EOG), eye-tracking techniques, and facial emotion encoding measurements known in the art. Generally, such biofeedback sensors and associated techniques measure the body's responses to brain stimuli, which in the present invention, are predetermined audio and/or visual food representations 600. Inventively, the present invention utilizes the user's bodily responses to such brain stimuli to objectively determine user food preferences for generating an individualized diet plan.

Figure 8:
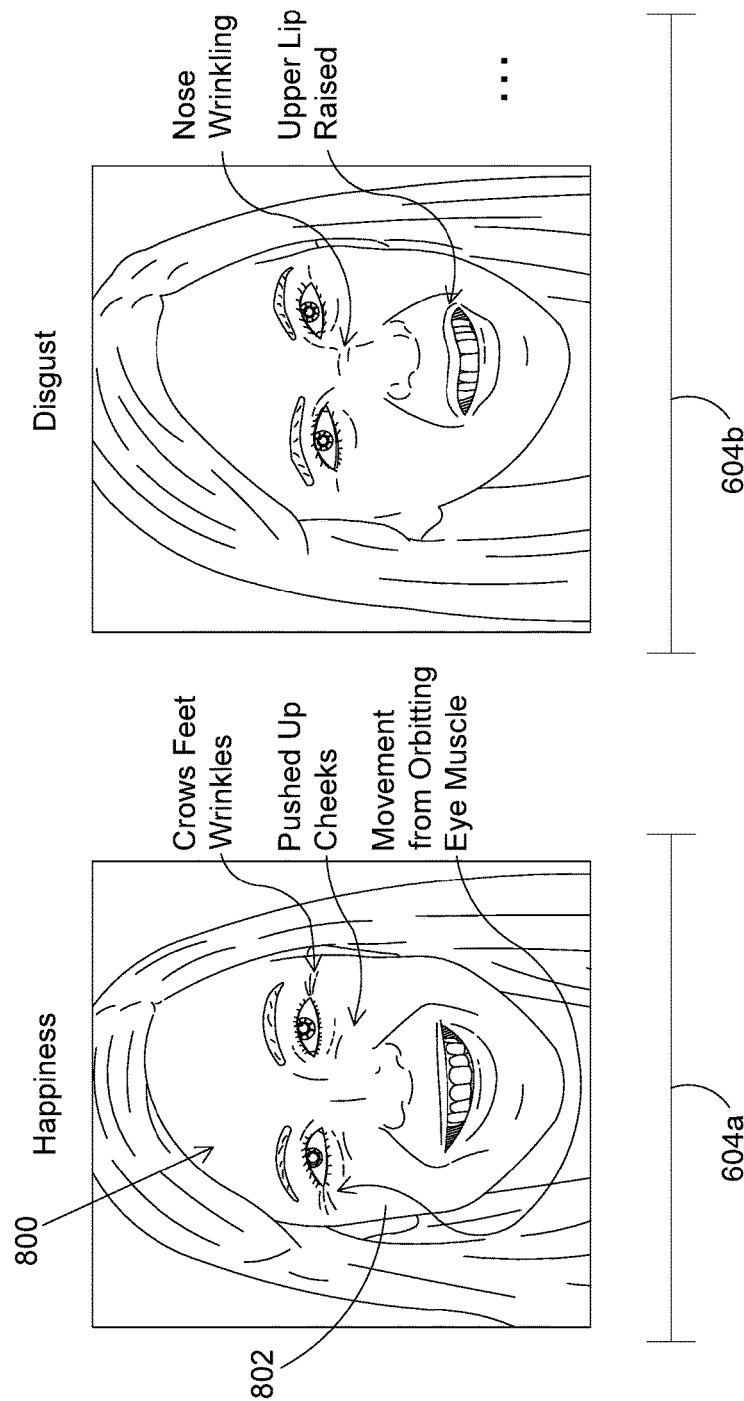
FIG. 8 is a sequence of user-responses captured by the camera in accordance with an embodiment of the present invention.
Figure 9:
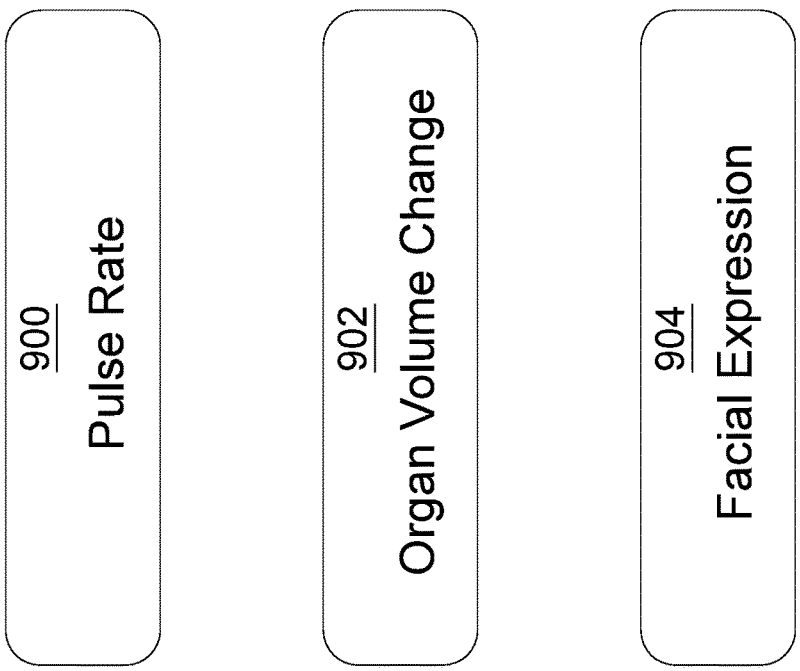
FIG. 9 is a block diagram of a plurality of interpretation modules used to interpret the captured user-responses to determine the user's food preference in accordance with embodiments of the present invention.

In the exemplary embodiment depicted in FIG. 8, the camera 200 captures a plurality of facial images, depicting various facial responses (e.g., pushed up cheeks and movement from muscles that orbit the eye or nose wrinkling and raised upper lip). The facial responses can correspond to a user's emotional response. For example, pushed up cheeks and movement of muscles that orbit the eye typically indicate happiness; while nose wrinkling and raising of the upper lip is associated with an emotion of disgust. Such objectively determined emotional responses can indicate the user's emotional association with a depicted food item, which may be a negative emotional response, a positive emotion response, or a neutral emotional response.

In step 310, each of the visual user-responses captured during the predetermined objective food preference determination period 602 is stored in the memory 206. In step 312, each of the stored visual user-responses 800 may be retrieved from the memory 206 and interpreted by the processing device 208 to determine a user-food preference for each of the plurality of predetermined audio and visual food representations 600. In one embodiment, the step of interpreting the visual user-responses 800 to determine a user-food preference may be performed after the predetermined objective food preference determination period 602. The user-food preference should be considered a subjective personal food preference of the user that is objectively determined according to the biofeedback techniques described herein and otherwise known in the art. In one embodiment, the user-food preference may be a like or a dislike. In another embodiment, the user-food preference may be categorized as a positive, negative, or neutral emotional response. In additional embodiments, the user-food preference may be a scoring system in which more points may indicate an increased level of distaste for the food item. It should be understood that various techniques and methods may be used to determine the user-food preference of the user according to the biofeedback data provided by the camera 200 and/or other sensors disposed on the personal computing device 104. Additional sensors may include, but are not limited to, pressure sensors, motion sensors, pulse rate sensors, temperature sensors, and the like. In some embodiments, the camera 200 may be operably configured so as to operate as one or more of such additional sensors (e.g., the camera 200 can be configured to be a motion sensor and a pulse rate sensor, an IR camera can be operable as a temperature sensor, etc.).

In one embodiment, a pulse of the user is determined by interpreting the visual user-response 800 captured during the respective the time interval 604. The pulse of the user may be depicted in the captured visual user-responses 800 of the user. In one embodiment, the pulse of the user may include a pulse wave associated with the user with parameters such as, for example, amplitude, speed, and/or frequency of cardiatric intervals, etc. In another embodiment, the pulse of the user may be considered a pulse rate of the user. In another embodiment, the memory 206 and/or memory disposed on the processing device 208 may store a pulse rate module 900. The pulse rate module 900 may be considered a logical module or process operable to allow the processing device 208 to execute the techniques for determining the pulse rate of the user.

In one embodiment, a change in volume of an organ of the user is determined by interpreting the visual user-response 800 captured during the respective the time interval 604. The change in volume of the organ of the user may be depicted in the captured visual user-responses 800 of the user. In one embodiment, video plethysmography may be used to monitor the changes in the speed of pulse undulations from, for example, at least four facial angles captured by the camera 200 during the respective time interval 604. In another embodiment, the memory 206 and/or memory disposed on the processing device 208 may store an organ volume change module 902. The organ volume change module 902 may be considered a logical module or process operable to allow the processing device 208 to execute the techniques for determining the rate of change of the volume of an organ of the user.

In one embodiment, a facial expression of the user is determined by interpreting the visual user-response 800 captured during the respective the time interval 604. The facial expression of the user may be depicted in the captured visual user-responses 800 of the user. In one embodiment, at least nine facial control points may be used to monitor the changes in the user's facial expression captured by the camera 200 during the respective time interval 604. In another embodiment, the memory 206 and/or memory disposed on the processing device 208 may store a facial expression module 904. The facial expression module 904 may be considered a logical module or process operable to allow the processing device 208 to execute the techniques for determining the user's facial expression as a result of being exposed to a food item.

In additional embodiments, other logical modules or techniques may be used to interpret the biological feedback captured by the camera 200 (and/or other biometric sensors) so as to objectively determine the user-food preference associated with the respective food item. Advantageously, the technical field of dietary software is improved by allowing computing devices to objectively determine a personal food preference of a dieter, which may elude the dieter's conscious mind. Most conventional diet plans begin with the assumption that the dieter will consciously know what he or she likes and does not like. Accordingly, conventional dietary software allows the user to either input their likes and dislikes, or allows the user to choose from a wide range of menu options, or alternatively merely prescribes a general non-individualized dietary plan of healthy foods, without any consideration of the individual dieter's food preferences. Contrary to conventional dietary software, the present invention assumes that the dieter is consciously unaware of at least some of his/her food preferences, which may be sabotaging his/her dieting efforts. Further, contrary to conventional dietary software, embodiments of the present invention do not require user inputs, other than a start command to begin the predetermined objective food preference determination period 602. With a single user-input command to begin the predetermined objective food preference determination period 602, a software application associated with the present invention may be able to objectively determine user-food preferences without ever having to ask the dieter.

Figure 10:
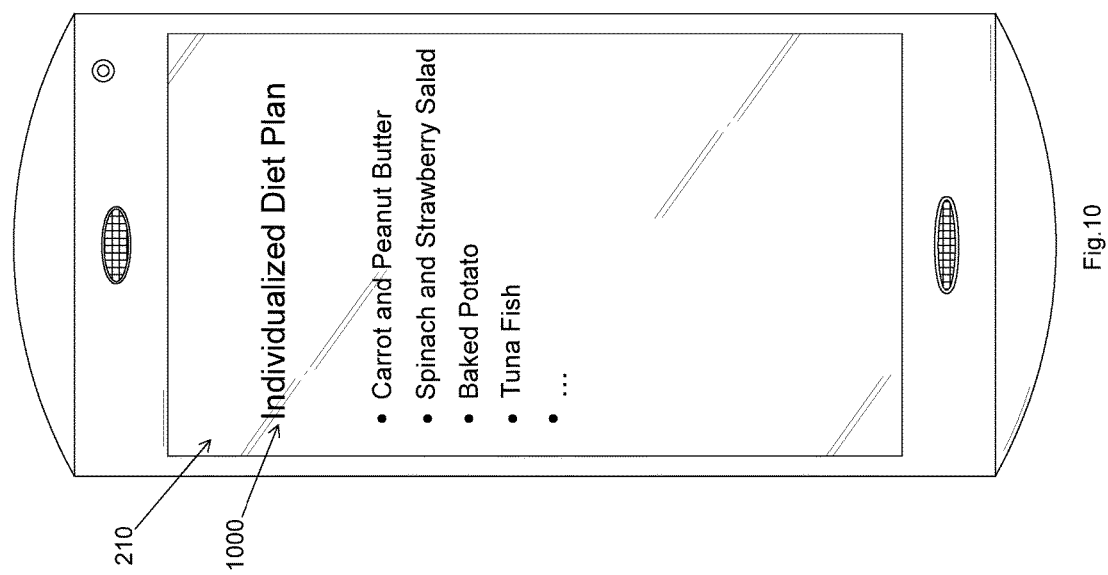
FIG. 10 is a screenshot from the exemplary software application of FIG. 4 depicting an individualized diet plan generated based on the user's food preferences in accordance with an exemplary embodiment of the present invention.
Figure 11:
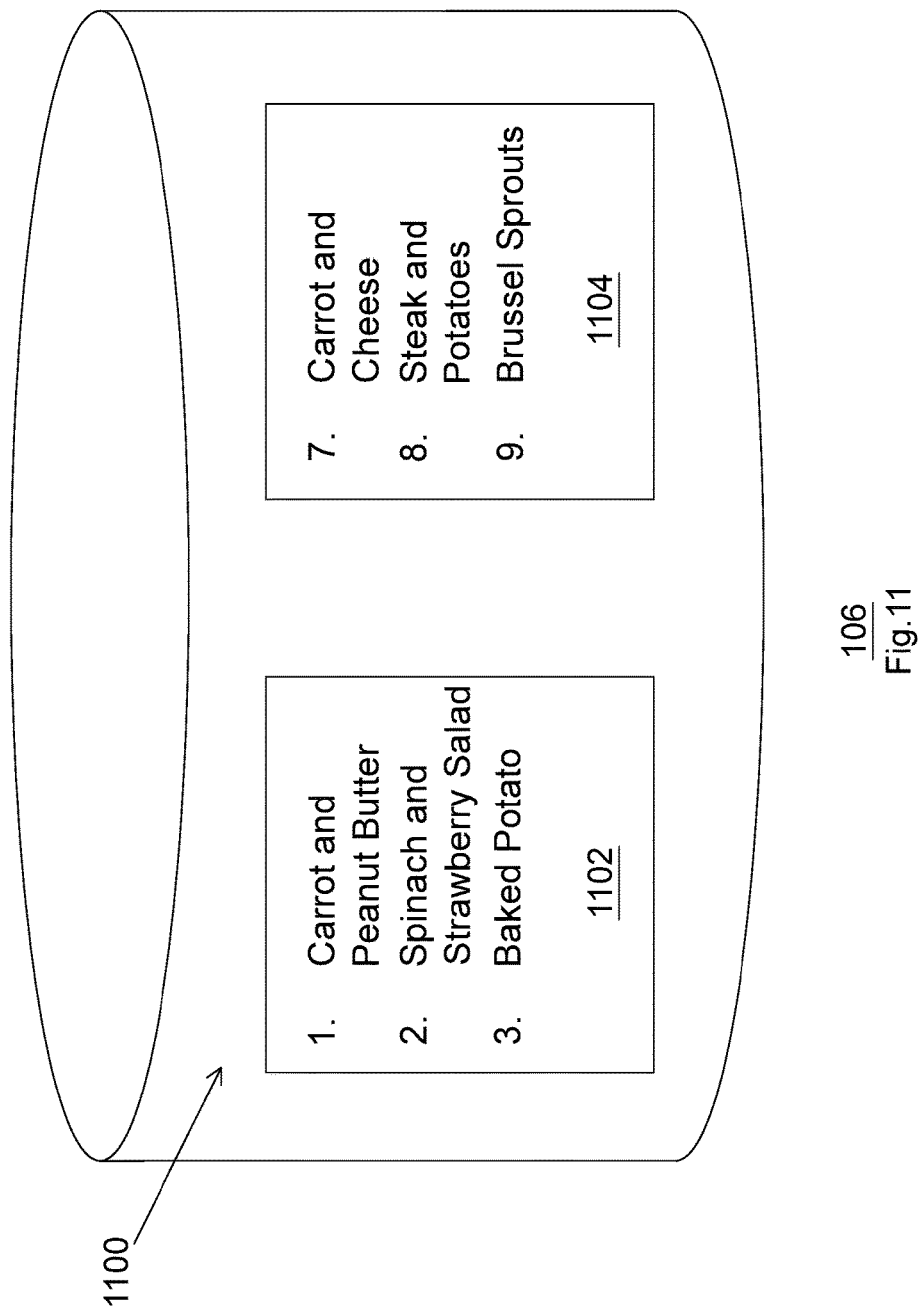
FIG. 11 is a block diagram of the server/database of FIG. 1 storing subsets of food items thereon, each subset corresponding to a category of user food preferences in accordance with an embodiment of the present invention.
Figure 12:
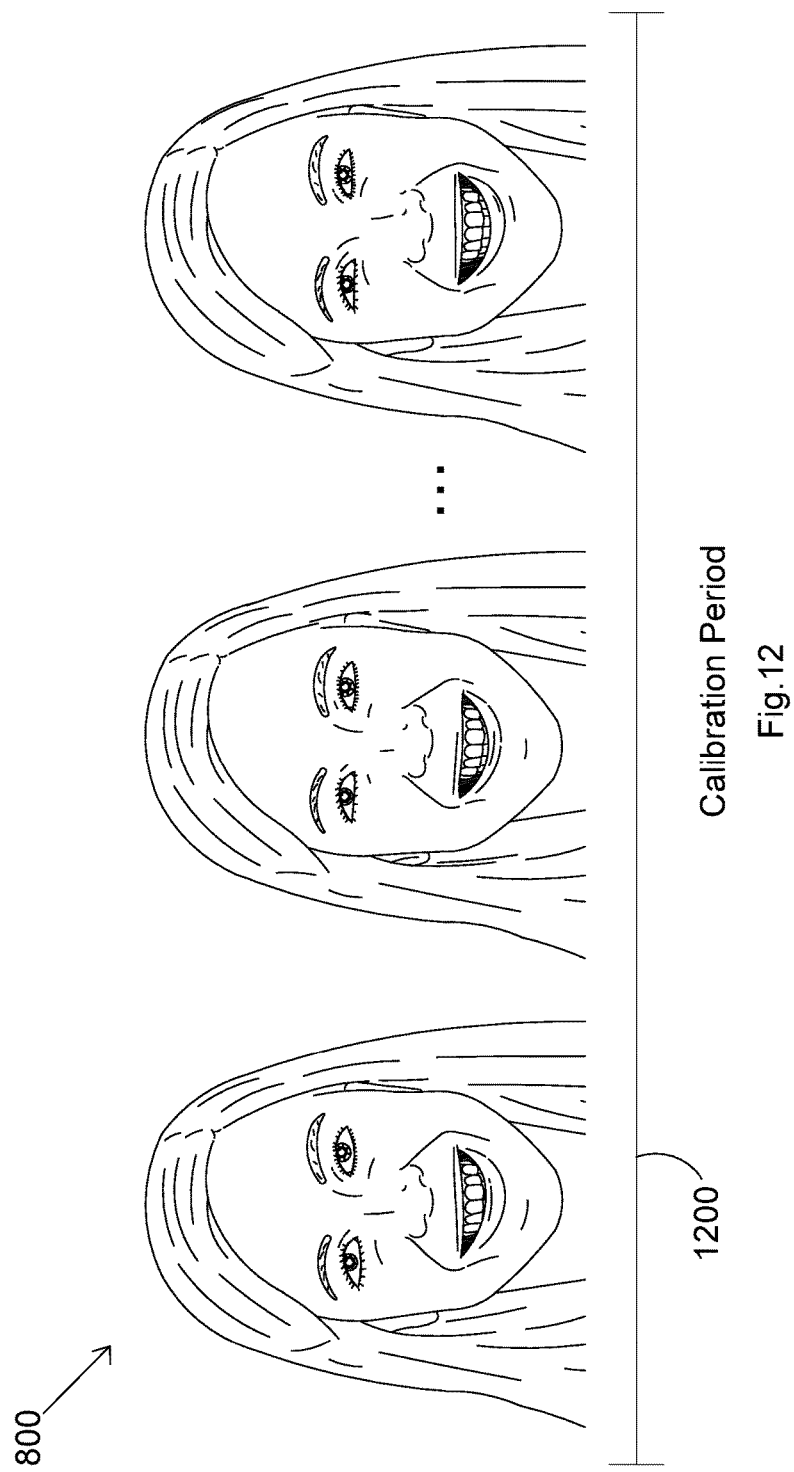
FIG. 12 is a sequence of user-responses captured by the camera during a calibration period to establish a baseline user response in accordance with an embodiment of the present invention.

In step 314, an individualized diet plan 1000 for the user is generated based on the user-food preferences determined in step 312. As depicted in FIG. 10, the individualized diet plan 10000 may be displayed on the display 210 for the user to view. In one embodiment, the database 106 may store a plurality of predetermined food items 1100 thereon from which the individualized diet plan 1000 may be generated. Accordingly, the individualized diet plan 1000 may include a list of food items selected from a first subset 1102 of the plurality of food items 1100 stored on the database 106. The first subset 1102 of food items 1100 may include food items 1100 that were determined to have a user-food preference that is associated with a positive or a neutral user-response. There may also be a second subset 1104 of food items 1100 stored on the database 106, which may be considered mutually exclusive from the first subset 1102 of food items 1100. The second subset 1104 of food items 1100 stored on the database 106 may be food items 1100 that were determined to have a user-food preference that is associated with a negative user-response. In one embodiment, the individualized diet plan 1000 may only include food items from the first subset 1102, having positive or neutral user-responses. Stated another way, the individualized diet plan 1000 may be generated to expressly exclude food items from the second subset 1104, having the negative user-responses. In a further embodiment, the user may also be expressly instructed to exclude such negatively-associated food items from the user's diet for a particular time period, e.g., one to six weeks.

In another embodiment, the individualized diet plan 1000 is generated by hierarchically ranking each food item 1100 stored on the database 106 and presented to the user during the predetermined objective food preference determination period 602. In one embodiment, the hierarchical ranking may be based on a hierarchal level of the user-food preference. In a further embodiment, points may be assigned to determine a hierarchal level. For example, a higher point value may be assigned to a food item associated with a user-response of an expansive smile than a food item associated with a user-response of a weak social smile. As a further example, a lower point value may be assigned to a user-response associated with disgust than a point value assigned to a user-response depicting a sad face. Additional techniques and methods for hierarchically ranking food items 1100 according to the user-response may also be employed in other embodiments of the present invention.

In one embodiment, before the predetermined objective food preference determination period 602, there may be provided a predetermined user calibration period 1200. During the predetermined user calibration period 1200, the camera 200 may automatically capture at least one visual user-response 800 of the user to establish a baseline user-response. In one embodiment, calibration may include objective measurements of pulse indexes (e.g., pulse waves with the attributes of amplitude, speed, frequency of cardiac intervals, etc.) obtained from the at least one visual user-response 800 of the user captured by the camera 200 during the predetermined user calibration period 1200. In a further embodiment, calibration may also include respiratory undulation, tissue saturation with oxygen, distribution of the registered parameters of the pulse wave coming from at least four areas (forehead in a left and a right projection, left and right cheek areas), facial skin, analysis of the geographic coordinates of the face control points (from the image captured by the camera 200), asymmetry of the emotional micro expressions of the facial muscles (expressions), and the like, obtained from the at least one visual user-response 800 of the user captured by the camera 200 during the predetermined user calibration period 1200. Such obtained results of the objective measurements may be considered to establish a baseline and are personalized for each and every user. In one embodiment, each new test begins with the predetermined user calibration period 1200. In one embodiment, the predetermined user calibration period 1200 may be between 5 and 10 seconds. In alternative embodiments, the predetermined user calibration period 1200 may be outside of this range.

The personal computing device 102 may also interpret the visual user-responses 800 captured during the predetermined user calibration period 1200 to determine the baseline user response. In a further embodiment, the interpreting step 312 may include interpreting the user-responses 800 captured during the predetermined objective food preference determination period 602 based on the baseline user response established during the predetermined user calibration period 1200. Stated another way, the objective user-response to the food product stimuli (during the predetermined objective food preference determination period 602) may be determined by the ideomotoric reaction of the user's facial muscles registered by the control of the micro-expressions of emotions in the control points in response to a food stimulus associated with the change in an amplitude and speed of a pulse wave, a change in the correlational dependence of the dynamics of the blood saturation of the areas on the facial skin, and the like. In other words, the user's reactions to the food stimuli are compared with the calibration data. In a further embodiment, statistical data on the user responses to the food stimuli may be saved and can be accessed and used later for future analysis and the development of individualized dietary recommendations.

Figure 13:
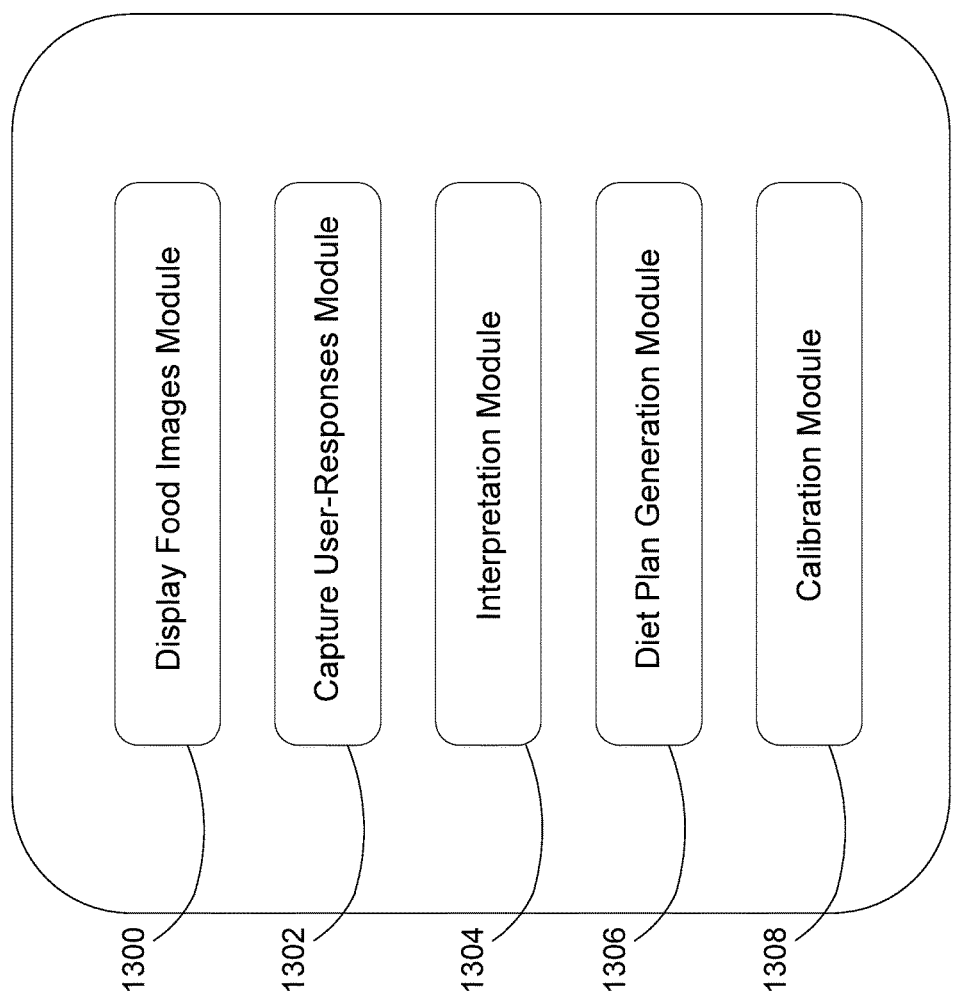
FIG. 13 is a block diagram of a plurality of logical structures performing various steps of the inventive process in accordance with an embodiment of the present invention.

FIG. 13 depicts a plurality of logical modules. Each logical module may include a set of computer instructions for executing various techniques and processes described herein. In the exemplary embodiment, there may be provided, for storage on, for example, the memory 206, a display food images module 1300, a capture user-responses module 1302, an interpretation module 1304, a diet plan generation module 1306, and a calibration module 1308. In one embodiment, the display food images module 1300 may perform step 306 of the computer-implemented process described with reference to the flow chart depicted in FIG. 3. Likewise, the capture user-responses module 1302 may perform the capturing user-responses step 308; the interpretation module 1304 may perform the interpreting step 312; the diet plan generation module 1306 may perform the generating the individualized diet plan step 314; and the calibration step described with reference to FIG. 12 may be performed by the calibration module 1308. As is understood in the art, these modules may be considering computer programming logic modules that are executed by a processing device, such as, the processing device 208. The process immediately ends at step 316.

A novel and efficient computer-implemented method and system has been disclosed that objectively determines a user's personal food preferences based on exposing the user to audio and/or visual food stimuli and detecting the user's biological responses via biological sensors, or, more specifically, psycho-physiological sensors. Embodiments of the invention provide for generating a personalized diet plan for the user that eliminates food items that are objectively determined to be distasteful to the user, or that the user otherwise has a negative association with. In addition, embodiments of the invention provide for exposing the user to a plurality of audio and/or visual food stimuli within a predetermined food display period, via the user's personal computing device, in very short time intervals in order to obtain the user's most instinctive biological response to the food stimuli.

What is claimed is:

1. A computer-implemented method of objectively determining a user's personal food preferences for an individualized diet plan, the method comprising the steps of:

providing a personal computing device including a processing device, a digital camera, a memory, a computer display, and a user-input interface communicatively coupled to one another;

executing a set of computer program instructions stored in the memory by the processing device to receive, by the user-input interface, an indication from a user to begin a predetermined objective food preference determination period;

initiating a user calibration period that includes the capturing, by the digital camera, of at least one digital facial image depicting a visual user-response unexposed to a plurality of predetermined digital food images, generating a plurality of facial geometric control points on the at least one digital facial image, and ascertaining, through the digital camera, a first facial blood saturation of at least one area of the user's facial skin when unexposed to the plurality of predetermined digital food images;

after the user calibration period and during the predetermined objective food preference determination period, reading data representing a plurality of predetermined digital food images stored in a database communicatively coupled to the processing device and automatically display, on the computer display of the personal computing device, each of the plurality of predetermined digital food images at equal time intervals that are less than or approximately equal to 0.385 seconds;

during each of the equal time intervals, automatically capturing, by the digital camera, at least one digital facial image having a second facial blood saturation of the at least one area of the user's facial skin and geometric facial points depicting at least one visual user-response of the user as emotive biofeedback data responsive to each predetermined digital food image displayed on the computer display during the predetermined objective food preference determination period;

storing, in the memory, the emotive biofeedback data for each of the at least one visual user-responses captured during each of the equal time intervals within the predetermined objective food preference determination period;

converting, by the processing device of the personal computing device, the emotive biofeedback data, through a comparison of the first and second facial blood saturations of the at least one area of the user's facial skin to ascertain a blood saturation change and a comparison of the plurality of facial control points on the user during the user calibration period with the geometric facial points of the digital facial image having during the objective food preference determination period to ascertain asymmetry, into emotional response data to obtain an objectively determined emotional response by the user to each predetermined digital food image displayed on the computer display;

interpreting, by the processing device of the personal computing device, data representing the objectively determined emotional response to each predetermined digital food image displayed on the computer display to determine a user-food preference for each predetermined digital food image displayed on the computer display; and after determining the user-food preference for each predetermined digital food image, generating, by the processing device of the personal computing device, an individualized diet plan for the user based on the determined user-food preference for each predetermined digital food image.

2. The computer-implemented method in accordance with claim 1, wherein:
each of the equal time intervals are between 0.233 and 0.385 seconds.

3. The computer-implemented method in accordance with claim 2, wherein:
each of the plurality of predetermined digital food images is formed as a computer displayable image in which a single food item occupies a substantial portion of the entire computer displayable image.

4. The computer-implemented method in accordance with claim 3, wherein:
the digital camera is operable to capture at least one image of the at least one visual user-response with a pixel resolution of at least 640×480 pixels.

5. The computer-implemented method in accordance with claim 1, further comprising:
prompting, by the personal computing device, the user to be physically disposed in front of a camera lens of the digital camera within a single separation distance from the camera lens and simultaneously within a viewing distance of the computer display during the entire predetermined objective food preference determination period.

6. The computer-implemented method in accordance with claim 1, wherein:
the step of automatically displaying each of the plurality of predetermined digital food images, further comprises a step of automatically displaying each of the plurality of predetermined digital food images in a continuous sequence during the predetermined objective food preference determination period.

7. The computer-implemented method in accordance with claim 1, wherein the step of generating the individualized diet plan further includes a step of:

generating a list of food items to exclude from the user's Individualized diet plan, the list of food items including at least one food item depicted in the plurality of predetermined digital food images displayed on the computer display during the predetermined objective food preference determination period that were determined, during the interpreting step, to have a user-food preference associated with a negative emotional user-response.

8. The computer-implemented method in accordance with claim 1, wherein the database includes a plurality of predetermined food items stored thereon from which the individualized diet plan is generated in the generating step, and wherein the step of generating the individualized diet plan further comprises the step of:

hierarchically ranking, by the processing device, each food item depicted in the plurality of digital food images displayed on the computer display during the automatically displaying step, the hierarchical ranking based on a hierarchal level of the user-food preferences determined in the interpreting step.

9. The computer-implemented method in accordance with claim 1, further comprising a step of at least one of:

determining a pulse of the user during each of the equal time intervals from the emotive biofeedback data captured during the respective equal time interval.

10. The computer-implemented method in accordance with claim 1, wherein:

each of the equal time intervals are equally-spaced apart from one another.

11. The computer-implemented method in accordance with claim 1, further comprising steps of:

before the predetermined objective food preference determination period, during a predetermined user calibration period, automatically capturing, by the digital camera disposed at the personal computing device, at least one visual user-response of the user; and interpreting, by the processing device of the personal computing device, the at least one visual user-responses captured during the predetermined user calibration period to determine a baseline user response, wherein each of the user-food preferences determined during the interpreting step of the predetermined objective food preference determination period is determined based on the baseline user response.

12. A computer-implemented method of objectively determining a user's personal food preferences for an individualized diet plan, the method comprising the steps of:

on a personal computing device including a processing device, a digital camera, a memory, a computer display, and a user-input interface, and a speaker communicatively coupled to one another, executing a set of computer program instructions stored in the memory by the processing device to:

receive, by the user-input interface, an indication from a user to begin a predetermined objective food preference determination period;

initiate a user calibration period that includes the capturing, by the digital camera, of at least one digital facial image depicting a visual user-response unexposed to a plurality of predetermined digital food images, generating a plurality of facial control points on the at least one digital facial image, and ascertaining, through the digital camera, a first facial blood saturation of at least one area of the user's facial skin when unexposed to the plurality of predetermined digital food images;

during the predetermined objective food preference determination period, read data representing a plurality of audio and visual food representations stored in a database communicatively coupled to the processing device and at least one of automatically displaying, on the computer display of the personal computing device, each of the plurality of predetermined visual food representations and automatically emitting, via the speaker, the plurality of predetermined audio food representations, at equal time intervals that are less than or approximately equal to 0.385 seconds;

during each of the equal time intervals, automatically capture, by at least one of the digital camera and the speaker, at least one digital facial image having a second facial blood saturation of the at least one area of the user's facial skin and geometric facial points depicting at least one user-response of the user as emotive biofeedback data responsive to each of the plurality of predetermined audio and visual food representations;

convert, by the processing device of the personal computing device, the emotive biofeedback data, through a comparison of the first and second facial blood saturations of the at least one area of the user's facial skin to ascertain a blood saturation change and a comparison of the plurality of facial control points on the user during the user calibration period with the geometric facial points of the digital facial image having during the objective food preference determination period to ascertain asymmetry, into emotional response data to obtain an objectively determined emotional response by the user to each of the plurality of predetermined audio and visual food representations;

interpret, by the processing device of the personal computing device, data representing the objectively determined emotional response to each of the plurality of predetermined audio and visual food representations to determine a user-food preference for each of the plurality of predetermined audio and visual food representations; and after determining the user-food preference for each of the plurality of predetermined audio and visual food representations generate, by the processing device of the personal computing device, an individualized diet plan for the user based on the determined user-food preference for each of the plurality of audio and visual food representations.

13. The computer-implemented method in accordance with claim 12, wherein:

each of the equal time intervals are between 0.233 and 0.385 seconds.

14. The computer-implemented method in accordance with claim 12, further comprising the step of:

prompting the user to be physically disposed in front of a camera lens of the digital camera within a single separation distance from the camera lens and simultaneously within at least one of a viewing distance of the computer display and a listening distance from the speaker during the entire predetermined objective food preference determination period.

15. The computer-implemented method in accordance with claim 14, wherein:

each of the at least one of the plurality of audio and visual food representations includes a plurality of predetermined digital food images formed as a computer displayable image in which a single food item occupies a substantial portion of the entire computer displayable image.

16. The computer-implemented method in accordance with claim 15, wherein:
the digital camera is operable to capture at least one image of the at least one user-response with a pixel resolution of at least 640×480 pixels.

17. A system for objectively determining a user's personal food preferences for an individualized diet plan, the system comprising:
at least one database storing at least one of a plurality of predetermined audio and visual food representations; and
a personal computing device communicatively coupled to the at least one database and including a processing device, a computer display, a speaker, a non-transitory memory, a user-input interface, and a digital camera communicatively coupled to one another and having a set of computer instructions stored in the non-transitory memory and executable by the processing device, the set of computer instructions including instructions for:
receiving, by the user-input interface on the personal computing device, an indication from a user to begin a predetermined objective food preference determination period;
initiating a user calibration period that includes the capturing, by the digital camera, of at least one digital facial image depicting a visual user-response unexposed to a plurality of predetermined digital food images, generating a plurality of facial control points on the at least one digital facial image, and ascertaining, through the digital camera, a first facial blood saturation of at least one area of the user's facial skin when unexposed to the plurality of predetermined digital food images;
during the predetermined objective food preference determination period, read data representing at least one of a plurality of predetermined audio food representations and a plurality of visual food representations stored in the at least one database and at least one of automatically displaying, on the computer display of the personal computing device, each of the plurality of predetermined visual food representations and automatically emitting, via the speaker, the plurality of predetermined audio food representations, at equal time intervals that are less than or approximately equal to 0.385 seconds;
during each of the equal time intervals, automatically capturing, by the digital camera, at least one digital facial image having a second facial blood saturation of the at least one area of the user's facial skin and geometric facial points depicting at least one user-response of the user as emotive biofeedback data responsive to each of the at least one of the plurality of predetermined audio and visual food representations output during the predetermined objective food preference determination period;
storing, in the non-transitory memory, the emotive biofeedback data for each of the at least one user-responses captured during each of the equal time intervals within the predetermined objective food preference determination period;
converting, by the processing device of the personal computing device, the emotive biofeedback data, through a comparison of the first and second facial blood saturations of the at least one area of the user's facial skin to ascertain a blood saturation change and a comparison of the plurality of facial control points on the user during the user calibration period with the geometric facial points of the digital facial image having during the objective food preference determination period to ascertain asymmetry, into emotional response data to obtain an objectively determined emotional response by the user to each predetermined digital food image displayed on the computer display;
interpreting, by the processing device, data representing the objectively determined emotional response to each of the plurality of predetermined audio and visual food representations to determine a user-food preference for each of the at least one of the plurality of predetermined audio and visual food representations;
after determining the user-food preference for each of the plurality of predetermined audio and visual food representations generating, by the processing device, an individualized diet plan for the user based on the determined user-food preference for each of the at least one of the plurality of predetermined audio and visual food representations; and
displaying, on the computer display, the individualized diet plan.

18. The system in accordance with claim 17, wherein:
each of the equal time intervals are between 0.233 and 0.385 seconds.

19. The system in accordance with claim 18, wherein:
each of the at least one of a plurality of predetermined visual food representations is formed as a computer displayable image in which a single food item occupies a substantial portion of the entire computer displayable image.

20. The system in accordance with claim 19, wherein:
the digital camera is operable to capture at least one image of the at least one user-response with a pixel resolution of at least 640×480 pixels.

* * * * *